United States Patent [19]

Krasnobajew et al.

[11] 4,066,504

[45] Jan. 3, 1978

[54] ALIPHATIC DIALDEHYDE-AROMATIC POLYAMINE CONDENSATION PRODUCTS BOUND TO PROTEINS AND ENZYMES

[75] Inventors: Victor Krasnobajew, Zollikerberg; Regula Böeniger, Greifensee, both of Switzerland

[73] Assignee: Givaudan Corporation, Clifton, N.J.

[21] Appl. No.: 714,153

[22] Filed: Aug. 13, 1976

Related U.S. Application Data

[62] Division of Ser. No. 593,605, July 7, 1975, abandoned.

[30] Foreign Application Priority Data

July 9, 1974 Switzerland ................ 9415/74
June 11, 1975 Switzerland ................ 7543/75

[51] Int. Cl.$^2$ .................................. C12K 1/00
[52] U.S. Cl. ............................. 195/63; 195/68; 195/DIG. 11; 260/6; 260/52; 260/72.5; 260/112 R
[58] Field of Search ........... 260/52, 6, 112 R, 72.5; 195/63, 68

[56] References Cited

U.S. PATENT DOCUMENTS

| 3,503,739 | 3/1970 | Dubosc et al. ........... 260/72.5 |
| 3,598,748 | 8/1971 | Hirosawa ................ 260/72.5 |
| 3,681,297 | 8/1972 | D'Alelio ................. 260/72.5 |
| 3,706,633 | 12/1972 | Katchalski et al. ......... 195/63 |
| 3,839,265 | 10/1974 | Meyer-Stoll ............. 260/37 N |
| 3,959,079 | 5/1976 | Mareschi et al. ............ 195/63 |

FOREIGN PATENT DOCUMENTS

| 993,955 | 11/1951 | France. |
| 131,027 | 10/1970 | Netherlands. |
| 401,535 | 10/1933 | United Kingdom. |
| 1,089,148 | 11/1967 | United Kingdom. |
| 1,210,300 | 10/1970 | United Kingdom. |
| 1,398,294 | 6/1975 | United Kingdom. |

OTHER PUBLICATIONS

Chem. Absts. 82 (1975) 17157x, "Polymerization of Acrolein with Amines," Shim et al.

*Primary Examiner*—Edward M. Woodberry
*Attorney, Agent, or Firm*—Thomas Cifelli, Jr.; Robert F. Tavares

[57] ABSTRACT

Polymeric condensation products obtained by condensing specified amines and aldehydes have high activity to fix, i.e, insolubilize, proteins, including enzymes.

16 Claims, No Drawings

ALIPHATIC DIALDEHYDE-AROMATIC POLYAMINE CONDENSATION PRODUCTS BOUND TO PROTEINS AND ENZYMES

This is a division, of application Ser. No. 593,605 filed July 7, 1975, now abandoned.

FIELD OF THE INVENTION

This invention relates to the field of insolubilizing proteins.

RELATED APPLICATIONS

This application is related to pending U.S. patent applications, Ser. No. 440,438, filed Feb. 7, 1974, and Ser. No. 571,187, filed Apr. 24, 1975. The latter application is a divisional application of Ser. No. 440,438.

The aforesaid two applications, as well as Ser. No. 593,605, filed July 7, 1975, of which the present application is a divisional, all have been abandoned.

Copending application, Ser. No. 605,965 filed Aug. 19, 1975 is a continuation-in-part of applications Ser. Nos. 440,438 and 571,187.

The relationship of this application to the other two applications is as to related subject matter. A clear line of distinction exists as to the claims in all three applications.

PRIOR ART

The manufacture of a condensation resin having a large bonding capacity for proteins, by the reaction of 1,3-phenylenediamine and formaldehyde, as well as diazotisation of the reaction product, is known.

It has surprisingly been found, in accordance with the present invention, that a substantially more active product with respect to the fixing or insolubilizing of proteins is obtained when the novel condensation products of the present invention are used as carriers for the proteins.

SUMMARY OF THE INVENTION

It is known that proteins, especially enzymes, can be bonded to solid carrier materials to give insoluble products which have advantageous properties. The bonded, insolubilized, but biologically active, proteins can, for example, be more readily handled as in their natural soluble form. Because they can be readily recovered, enzymes bonded to a carrier can be used several times in a stationary process or, with particular advantage, in a process which is continuously worked.

Copending applications, Ser. Nos. 440,438 and 571,187, disclose and claim the novel condensation product obtained by reacting 1,3-diphenylenediamine with glutardialdehyde, which is distinguished by having a large bonding capacity for proteins.

The present invention is concerned with polymeric condensation products obtained by condensing a carbocyclic, aromatic polyamine with an aliphatic dialdehyde or acrolein, with the exception of the 1,3-phenylenediamine glutardialdehyde condensation product.

This invention is also concerned with a process for the manufacture of the foregoing polyaminealdehyde resins, which process comprises reacting a carbocyclic, aromatic polyamine or 3-methylmercaptoaniline with an aliphatic dialdehyde or acrolein to give a condensation product suitable for the fixing or insolubilizing of proteins (the manufacture of the 1,3-phenylenediamine glutardialdehyde condensation product being excluded). The invention is further concerned with a process for the fixing of proteins to these resins and with the proteins fixed to such resins.

Carbocyclic, aromatic polyamines which can be used in the process of the present invention include primary diamines or triamines, that is, mononuclear compounds such as phenylenediamines (e.g., p-phenylenediamine) and phenylenetriamines (e.g., 2,4,6-triaminophenol, 2,4,6-triaminotoluene), polynuclear, e.g., dinuclear compounds such as biphenyldiamines (e.g., benzidine) or polynuclear compounds with aliphatic bridges, e.g., with up to 2 methylene bridges such as diaminodiphenylalkanes (e.g., diaminodiphenylmethanes).

Apart from amino groups, the aromatic nuclei can also carry other substituents such as halogen atoms (e.g., chlorine), lower alkyl groups (e.g., methyl, ethyl), lower alkoxy groups (e.g., methoxy, ethoxy) or hydroxy, carboxy, mercapto, lower alkylthio or sulphonyl groups.

Finally, mixtures of different polyamines can also be employed as reaction components in the manufacture of the condensation products in accordance with the invention.

Preferred polyamine reaction components are benzidine and 2,4,6-triaminotoluene.

Examples of aliphatic dialdehydes which can be used in the process of the present invention include dialdehydes with up to 6 carbon atoms, e.g., glutardialdehyde, succinic acid dialdehyde, glyoxal, etc. Glutardialdehyde is preferably used.

Whether or not the condensation products manufactured according to the process of the present invention are suitable for the fixing or insolubilizing of enzymes can be experimentally determined in a simple manner by treating the condensation product with an enzyme, preferably amyloglucosidase, and measuring the activity of the fixed enzyme. The suitability is verified if this activity comes to at least 50 to 100 units per gram of condensation product carrier material.

The following test procedure can be used for this purpose:

A chromatography column (1.5 × 15 cm) is filled with 1 g of the condensation product carrier material. A solution of 1 g of amyloglucosidase (50 units/mg) in 100 ml of 16 mmol acetate buffer (pH 4.8) is passed through the column at room temperature and with a flow rate of 20 ml per hour. As already mentioned, the fixed enzyme should have an activity of at least 50 to 100 units/g of carrier material.

The activity is measured by way of the glucose liberated from soluble starch [according to Zulkowsky]. The liberated glucose is determined enzymatically by means of the glucose-oxidase/peroxidase test [Bergmeyer, Methoden der enzymatischen Analyse, Volume I, (1970) page 416]. [1 unit = that amount of enzyme which liberates 1 μmol of glucose/min from soluble starch at a reaction temperature of 60° C and at pH 4.8].

Alternatively, the suitability is verified if the condensation product carrier material fixes at least 10 mg of a protein (e.g., beef serum albumin) per gram of carrier. The amount of fixed protein can be determined by hydrolyzing the carrier-fixed protein with 6-N hydrochloric acid and subsequently determining the amount of free amino acids with the aid of any practicable analysis method for amino acids.

Proteins which can be bonded to the condensation products in accordance with the present invention include polypeptides, antigens, antibodies, protein inhibitors and, especially, enzymes. The enzymes can be of vegetable, animal or microbial origin. The enzymes may be hydrolases (peptidases, proteinases, desaminases, carbohydrases, esterases, nucleases), lyases or desmolases (hydrolyases, decarboxylases, aldolases), transferases, isomerases, oxidoreductases and ligases. Examples of enzymes from which insoluble enzyme preparations provided by this invention can be manufactured are alcoholdehydrogenase, naringinase, hesperidinase, β-glucosidase, α-amylase, invertase, amyloglucosidase, urease; trypsin, ficin, papain, bromelin, subtilopeptidase, rennin, glucoseisomerase, glucoseoxidase, peroxidase, catalase, acylase, cytochrome, ribonuclease, phosphodiesterase and adenyldeaminase.

The molar ratio of the polyamine and aldehyde reaction partners expediently lies at between 1:1 and 1:10, a ratio of about 1:3 being preferred.

The reaction can be carried out in a manner known per se; for example, in aqueous solution, preferably with the addition of an acid such as a mineral acid (e.g., hydrochloric acid). In a particular embodiment, the reaction is carried out in the presence of an inert, fine-grained, preferably inorganic, especially silicate-containing, adjuvant. Examples of such adjuvants are silica gel, pumice-stone, diatomaceous earth (kieselguhr), bentonite, wollastonite, porous glass and also metal oxides such as aluminium oxide or hydroxylapatite. It is preferred to use silica gel (e.g., with a particle size of 0.05-0.2 mm, 70-325 mesh) or pumicestone (e.g., with a particle size of 0.05-10 mm). The presence of such an adjuvant gives rise to a homogeneous particle formation in the reaction and, as a result, an improved sedimentation is achieved. The reaction in the presence of an adjuvant is expediently carried out by initially bringing the particles into contact with one of the two reaction components and then adding the second component with simultaneous or subsequent slight acidification.

The reaction can be carried out in a homogeneous phase or, preferably, in a two-phase system with the addition of an acid such as a mineral acid (e.g., sulphuric acid, phosphoric acid or, preferably, hydrochloric acid) or an organic acid (e.g., a carboxylic acid such as acetic acid) with vigorous stirring or shaking. The use of a two-phase system promotes the formation of spherical, substantially homogeneous particles which are easy to filter and which sediment well, these particles being especially well suited as a carrier material. The reaction products are amorphous materials which are insoluble in water and the usual organic solvents.

Inert, water-immiscible organic solvents (e.g., dichloromethane, chloroform, carbon tetrachloride, benzene, toluene, ethyl acetate, dioxane, carbon disulphide) are suitable as the second phase. Chloroform is preferably used as the inert, water-immiscible solvent, but acetone is also suitable for this purpose.

The reaction temperature is not critical; it can lie, for example, at between 0° C and 50° C, preferably at room temperature (i.e., at about 18°-22° C). In accordance with the process provided by this invention there is obtained a condensation product carrier material which, although already very active, can be still further activated by diazotization. The diazotization can be carried out in a manner known per se by treatment with nitrite and acid.

In order to fix the protein to the carrier material, the latter is treated with an aqueous solution, preferably a buffered solution, of the protein (1-50 mg/ml) at a temperature of 0°-30° C, preferably 4° C to room temperature. This treatment can be carried out while stirring on shaking. Because of the high activity of the carrier material, the fixing of the proteins can also be advantageously carried out by simply filtering the protein solution through a carrier layer, preferably a column filled with the carrier material, as is common, for example, in column chromatography. Thus, for example, culture filtrates of microorganisms which contain proteins or enzymes can be allowed to run directly through a column of carrier material, the proteins or enzymes being selectively fixed to the carrier. The column is expediently rinsed with a buffer solution and 1-M potassium chloride solution in order to remove the non-fixed proteins.

The proteins fixed to the carrier material are generally very stable and very high specific activities (unit/g) are achieved in the case of enzymes. Loadings of, for example, 1:3—10 parts by weight of protein/carrier material are achieved.

The carrier-bonded proteins provided by this invention, especially enzymes, can be used in a manner known per se; for example, for analytical or preparative purposes or in food technology such as in the manufacture of glucose from starch [see, for example, Scientific American 224, (No. 3) 26–33 (1971); Angew. Chemie 84, (8) 319–268 (1972); chemiker Zeitung 96, (11), 595–602 (1972); C & EN, (15.2.71), 86–87].

In this important large-scale process, amylugucosidase fixed to the condensation product provided by the present invention can be utilised for the manufacture of glucose from the "glucose syrup" (prehydrolysed starch). The condensation products can then be transferred, for example, onto columns (fixed-bed process). A further application results in the enzymatic degradation of lactose in milk products by means of lactases (e.g., "sweets" from whey).

The following Examples illustrate the present invention. The quantitative data of the carrier material obtained or used is given with respect to dry weight.

EXAMPLE 1

To a solution or suspension of 5 g of the polyamine in 200 ml of chloroform, there are added portionwise with vigorous stirring, firstly 20 g of aldehyde (80 ml of a 25% solution in water) and, after a further 5 minutes, 20 ml of 7-N hydrochloric acid. The reaction mixture solidifies. It is treated with 300 ml of water and shaken for 5 minutes until it again becomes liquid. The polymeric particles are left to stand for 1 hour with occasional stirring. After vacuum filtration of the mixture over a Buchner funnel, the polymeric particles are washed with three 200 ml portions of acetone and then with 0.1-N sodium hydroxide solution. The residual chloroform is removed by washing with acetone. The thus obtained carrier particles are spherical, homogeneous and capable of good filtration; they are stored in water.

They can be employed for enzyme fixing, optionally after diazotization.

EXAMPLE 2

A chromatography column (1.5 × 15 cm) is filled with 1 g of carrier material and washed with the buffer solution used in the following enzyme fixing. The buffered enzyme solution (1-100 mg of protein per ml of buffer) is passed through the column with a flow rate of 20 ml/hour.

The coupling capacity is exhausted when protein can be detected in the eluate, which can be detected, for example, by measurement of the absorption spectrum at 280 mµ. The non-fixed enzyme is removed by washing the column with 1-M potassium chloride and the buffer solution. There then follows an activity determination of an aliquot of the enzyme-fixed material with the respective substrate under given reaction conditions. Then an aliquot of the enzyme solution is washed with water, dried and the dried material determined analogously. The number of units of enzyme activity/g of carrier material can be determined in this manner.

The condensation products manufactured according to Example 1 and their corresponding activities determined according to Example 2 are compiled in the following Table:

Table

| Condensation product | | Activity of the fixed enzyme, (amyloglucosidase activity) units/g of carrier material* | Amount of fixed enzyme (mg per g of carrier)* |
| --- | --- | --- | --- |
| Polyamine | Aldehyde | | |
| 1,4-Phenylenediamine | Glutardialdehyde | 800 | |
| 2,4,6-Triaminophenol | " | 800 | |
| 2,4,6-Triaminotoluene | " | 1400 | |
| 2,4-Diaminotoluene | " | 700 | |
| 2,4-Diaminoanisole | " | 4000 | |
| 3-Amino-4-chloroaniline | " | 820 | |
| 3-Methylmercaptoaniline | " | 500 | |
| Benzidine | " | 600 | |
| 4,4'-Diaminodiphenylmethane | " | 200 | ca. 50–200 |
| 4,4'-Diaminodiphenylsulphone | " | 250 | |
| Benzidine:1,3-phenylenediamine (1:3) | " | 500 (Glucoseoxidase) | |
| 1,3-Phenylenediamine | Glyoxal | 600 | |
| 1,3-Phenylenediamine | Succindialdehyde | 800 | |
| 1,3-Phenylenediamine | Acrolein | 600 | |

*Analogous results are obtained for catalase, β-galactosidase, subtilopeptidase, naringinase and α-amylase.

What is claimed is:

1. A process for the fixing or insolubilizing of proteins, which process comprises bonding a protein to a condensation product obtained according to the process which comprises reacting a carbocyclic, aromatic polyamine or 3-methylmercaptoaniline with an aliphatic dialdehyde having up to 6 carbon atoms or acrolein to give a condensation product suitable for the fixing or insolubilizing of proteins, excluding the manufacture of the 1,3-phenylenediamine-glutardialdehyde condensation product.

2. A process for the fixing or insolubilizing of enzymes, which process comprises bonding an enzyme to a condensation product obtained according to the process of claim 1.

3. A process according to claim 1, wherein the bonding is carried out using the column technique.

4. A process according to claim 2, wherein the bonding is carried out using the column technique.

5. A protein bonded to a condensation product obtained according to the process claimed in claim 1.

6. A protein bonded to a condensation product obtained according to the process claimed in claim 1, wherein 2,4-diaminoanisole is said amine and glutardialdehyde is said aldehyde.

7. A protein bonded to a condensation product obtained according to the process claimed in claim 1, wherein 2,4,6-triaminotolueme is said amine and glutardialdehyde is said aldehyde.

8. A protein bonded to a condensation product obtained according to the process claimed in claim 1, wherein benzidine is said amine and glutardialdehyde is said aldehyde.

9. A protein bonded to a condensation product obtained according to the process claimed in claim 1, wherein 1,3-phenylenediamine is said amine and acrolein is said aldehyde.

10. A protein bonded to condensation product obtained according to the process claimed in claim 1, wherein a mixture of benzidine and 1,3-phenylenediamine in the ratio 1:3 is said amine and glutardialdehyde is said aldehyde.

11. An enzyme bonded to a condensation product obtained according to the process claimed in claim 1.

12. An enzyme bonded to a condensation product obtained according to the process claimed in claim 1, wherein 2,4-diaminoanisole is said amine and glutardialdehyde is said aldehyde.

13. An enzyme bonded to a condensation product obtained according to the process claimed in claim 1, wherein 2,4,6-triaminotoluene is said amine and glutardialdehyde is said aldehyde.

14. An enzyme bonded to a condensation product obtained according to the process claimed in claim 1, wherein benzidine is said amine and glutardialdehyde is said aldehyde.

15. An enzyme bonded to a condensation product obtained according to the process claimed in claim 1, wherein 1,3-phenylenediamine is said amine and acrolein is said aldehyde.

16. An enzyme bonded to a condensation product obtained according to the process claimed in claim 1, wherein a mixture of benzidine and 1,3-phenylenediamine in the ratio 1:3 is said amine and glutardialdehyde is said aldehyde.

* * * * *